US010434312B2

(12) United States Patent
Goel

(10) Patent No.: US 10,434,312 B2
(45) Date of Patent: Oct. 8, 2019

(54) ELECTRODE ASSEMBLY FOR SPINAL CORD STIMULATION

(71) Applicant: Amitabh Goel, Lakewood Ranch, FL (US)

(72) Inventor: Amitabh Goel, Lakewood Ranch, FL (US)

(*) Notice: Subject to any disclaimer, the term of this patent is extended or adjusted under 35 U.S.C. 154(b) by 174 days.

(21) Appl. No.: 15/803,404

(22) Filed: Nov. 3, 2017

(65) Prior Publication Data
US 2018/0056070 A1 Mar. 1, 2018

(51) Int. Cl.
*A61N 1/36* (2006.01)
*A61N 1/05* (2006.01)
*A61B 5/00* (2006.01)
*A61N 1/04* (2006.01)

(52) U.S. Cl.
CPC ....... *A61N 1/36071* (2013.01); *A61N 1/0551* (2013.01); *A61N 1/0553* (2013.01); *A61N 1/36178* (2013.01); *A61B 5/4836* (2013.01); *A61N 1/0456* (2013.01); *A61N 1/36017* (2013.01); *A61N 1/36182* (2013.01)

(58) Field of Classification Search
CPC .............................. A61N 1/0553; A61N 1/0551
See application file for complete search history.

(56) References Cited

U.S. PATENT DOCUMENTS

| 6,895,280 | B2 | 5/2005 | Meadows et al. |
| 7,359,755 | B2 | 4/2008 | Jones et al. |
| 7,949,412 | B1 | 5/2011 | Harrison et al. |
| 7,987,000 | B2 | 7/2011 | Moffitt et al. |
| 8,019,441 | B2 | 9/2011 | Wallace et al. |
| 8,463,401 | B2 | 6/2013 | Jones et al. |
| 8,494,654 | B2 | 7/2013 | Pianca et al. |
| 8,588,936 | B2 | 11/2013 | MacDonald et al. |
| 8,612,018 | B2 | 12/2013 | Gillbe |
| 8,620,456 | B2 | 12/2013 | Goel |
| 8,798,769 | B1 | 8/2014 | Parker, Jr. |
| 8,892,215 | B2 | 11/2014 | Lipani |
| 9,114,249 | B2 | 8/2015 | Goel |
| 9,247,574 | B2 | 1/2016 | Wang et al. |
| 9,463,312 | B2 | 10/2016 | Staunton et al. |
| 9,492,655 | B2 | 11/2016 | Pianca et al. |
| 9,561,363 | B2 | 2/2017 | Skubitz et al. |

(Continued)

FOREIGN PATENT DOCUMENTS

| EP | 1518584 | 3/2005 |
| WO | WO2016090420 | 6/2016 |

*Primary Examiner* — David W Bates
(74) *Attorney, Agent, or Firm* — Kenneth H. Jack; Davis & Jack, L.L.C.

(57) ABSTRACT

An electrode assembly for stimulation of a spinal cord within a spinal canal, the spinal canal containing a dura mater, the assembly incorporating a base, a lateral arm extending from the base; a ventral series of electrodes attached to base and to the lateral arm; a dorsal series of electrodes attached to the base and to the lateral arm; ventral and dorsal matrices of electrical conductors respectively communicating electrically with the ventral and dorsal series of electrodes; and an electric pulse generator for electrifying the ventral and dorsal conductors, the generator being adapted for exclusively electrifying the ventral matrix of electrical conductors, and for alternatively exclusively electrifying the dorsal matrix of electrical conductors.

10 Claims, 5 Drawing Sheets

(56) References Cited

U.S. PATENT DOCUMENTS

| | | |
|---|---|---|
| 2005/0203600 A1 | 9/2005 | Wallace et al. |
| 2009/0099439 A1* | 4/2009 | Barolat .............. A61B 5/04001 |
| | | 600/372 |
| 2014/0066950 A1 | 3/2014 | MacDonald et al. |
| 2014/0088674 A1* | 3/2014 | Bradley ............... A61N 1/0553 |
| | | 607/117 |
| 2014/0200639 A1 | 7/2014 | DeLaRama |
| 2015/0094734 A1 | 4/2015 | Staunton et al. |
| 2016/0158539 A1 | 6/2016 | Moffitt et al. |
| 2016/0213915 A1* | 7/2016 | Amrani ................ A61N 1/0558 |
| 2016/0367797 A1 | 12/2016 | Eckermann |

* cited by examiner

ELECTRODE ASSEMBLY FOR SPINAL CORD STIMULATION

FIELD OF THE INVENTION

This invention relates to spinal cord electrical stimulation. More particularly, this invention relates to electrode head components of spinal cord stimulator assemblies.

BACKGROUND OF THE INVENTION

In order to deploy and insert an electrical stimulator device into a pain patient's spinal canal at a target pain reducing location, a Tuohy needle or cannula is commonly inserted between a pair of the patient's vertebrae. Such needle insertion is commonly precisely guided to assure that the needle's tissue lancing end angularly enters the patient's spinal epidural space without piercing the dura mater sheath which dorsally covers the spinal cord.

Upon such Tuohy needle insertion, an electrode head and wire lead assembly may be threaded therethrough to enter and travel along dorsal aspect of the patient's spinal epidural space. Commonly, such electrode head and lead assembly includes a relatively stiff steel stay which is temporarily received within a stay bore or socket, such stay extending through the electrode wire lead for driving engagement against the electrode head. A pushing action applied to the lead and stay at an input end of the Tuohy needle may effectively drive the electrode head along the spinal epidural space until the electrode head reaches the targeted electrical stimulation location over the patient's spinal cord.

In order to reduce tissue injury at the Tuohy needle injection site and along the travel path of the electrode head within the spinal canal, the selected Tuohy needle preferably is small gauge. Such needle preferably has an inside diameter between 1.3 mm and 1.7 mm, and such needle size imposes limits upon the span, width, or diameter of the electrode head which must initially pass through the needle's bore.

To accommodate for such size and inside diameter restrictions, conventional spinal cord stimulating electrode head components are known to comprise a longitudinally stacked series of cylindrical electrodes. Such electrode configuration maximizes electrode surface contact area for each electrode in accordance with the function, contact area=$(l)(d)(\pi)$ (where l=the longitudinal dimension of each cylindrically configured electrode and where d=the inside diameter of the Tuohy needle). However, a problem associated with such contact area maximizing cylindrical electrode configuration arises as a result of the electrodes' 360° arcs. Such cylindrical electrodes inherently provide some amount of ventral electrical contact with the pain patient's spinal dura mater. However, the majority of such electrodes' contact areas communicate electrically with the dorsally overlying tissues in the epidural space. Transmission of electrical pulses to such dorsally overlying tissues causes undesirable side effects such as wastage of electrical energy, localized pain, and cramping. In the cylindrical electrode configuration, useful pulses emanate only from electrodes' relatively small ventral contact surfaces.

The instant inventive electrode assembly for stimulation of a spinal cord solves or ameliorates problems and challenges described above by specially configuring a spinal cord stimulating an electrode head to include separately operable and opposing series of electrodes which are situated upon an invertible electrode head.

BRIEF SUMMARY OF THE INVENTION

The instant inventive electrode assembly is intended for use for targeted electrical stimulation of a pain patient's spinal cord. As a beneficial palliative effect, such electrical impulses may mask or block relatively intense and unpleasant neural pain impulses which would otherwise be conducted by the spinal cord. The instant inventive assembly constitutes a tool for effecting electrical stimulation of the spinal cord.

A preferred embodiment of the instant inventive assembly comprises a base element which preferably has a longitudinal extension from a posterior end to an anterior end. In the preferred embodiment, such longitudinal extension is sufficient to span in the direction of the patient's anteroposterior axis a target stimulation zone which dorsally overlies the patient's spinal cord.

Upon a Tuohy needle assisted insertion of the assembly's base component into a pain patient's dorsal epidural space, and upon travel of such component to the target location dorsally overlying the patient's spinal cord, a ventrally oriented portion or face of the base may be described, for purposes of structural orientation in relation to the human body, as the base's ventral side. Correspondingly, an antipodal or opposite side of the base may be described as the base's ventral side. Consonantly with the base's ascribed ventral and dorsal sides, right and left side or aspects of the base may be respectively described as the base's lateral and oppositely-lateral sides. In the preferred embodiment, the invention's base component is composed of a durable flexible plastic material having a high dielectric strength for electrically isolating conductors mounted upon and/or extending through such base.

A further structural component of the instant inventive assembly comprises a lateral arm which, similarly with the base component, has posterior and anterior ends, and has a longitudinal extension from the base's posterior end to the base's anterior end. Similarly with the base component, the lateral arm component has ventral and dorsal sides. A proximal or base end of the lateral arm is preferably fixedly attached to the base's lateral side, and such arm has a lateral distal extension therefrom. In a preferred embodiment, the lateral arm is composed of the same plastic material as the base component, and the fixed attachment of those two components preferably constitutes a whole formation or integrated joint which is fabricated in an electrode head plastic molding process.

A further structural component of the inventive assembly comprises a ventral series or plurality of electrodes which is fixedly attached to a surface selected from the group consisting of the base's ventral side and the lateral arm's ventral side. In a preferred embodiment, each electrode among the ventral series of electrodes is fixedly attached both to the base's ventral side and to the lateral arm's ventral side. Also in the preferred embodiment, each electrode among the ventral series of electrodes is rectangularly configured, the electrodes forming a longitudinally extending array along the longitudinal extensions of the base and the lateral arm. Such ventral electrodes are preferably spaced longitudinally apart from each other in order to allow for separate and independent electrical stimulation operation of each of the ventral electrodes. In the preferred embodiment, the ventral series of electrodes is either adhesively bonded to the base and/or the lateral arm, or is integrally molded with such components. Each of such electrodes preferably is composed of a durable, corrosion resistant, and electrically conductive material such as platinum.

A further structural component of the instant inventive assembly comprises a dorsal series of electrodes which is attached to the base's dorsal side and/or the lateral arm's dorsal side. In the preferred embodiment, the dorsal electrodes are configured, composed, and mounted similarly with the ventral electrodes.

Further structural components of the instant inventive assembly comprise ventral and dorsal matrices of electrical conductors or wires. In the preferred embodiment, such matrices respectively communicate electrically with the ventral and dorsal series of electrodes. The ventral matrix of electrical conductors preferably comprises a collection or bundle of wires in sufficient numbers to allow an extension of at least one of such wires to each of the ventral electrodes. The dorsal matrix of electrical conductors preferably comprises a separate collection of electrically conductive wires which are similarly extendable for communication with each of the dorsal electrodes. In the preferred embodiment, the ventral and dorsal matrices of electrical conductors are integrally molded as a part of and are incorporated into the base and/or lateral arm. Such integrated mounting of the conductors advantageously allows the plastic material through which the wires pass to act as an insulator which electrically isolates each wire from the others.

Further structural components of the instant inventive assembly comprise means for electrifying the posterior end of each of the wires among the ventral and dorsal matrices of electrical conductors. In a preferred embodiment, such means comprise either a subcutaneously implantable electrical pulse generator, or an externally mounted electrical pulse generator. In the preferred embodiment, the electrical pulse generator is adapted for selectively and exclusively transmitting electric pulse signals to the ventral matrix of electrical conductors, and to the ventral series of electrodes without the transmission of any electric pulse or signal to any of the dorsal electrodes.

During implantation of the instant inventive assembly, the assembly's base, lateral arm, and electrode components are commonly driven anteriorly over the dorsal aspect of a pain patient's spinal dura mater. Such driving action moves the assembly's anterior end in a tissue lancing action which extends the assembly through adipose and veinous tissues which reside within the patient's dorsal epidural space. Progressive anterior tissue lancing motion of the assembly against such veinous and adipose tissues may, on occasion, exert twisting or turning forces against the assembly's lateral arm, causing such arm and the base to rotate with respect to the patient's anteroposterior axis. Upon such rotation, the ventral electrode series may undesirably travel to an angular orientation at which it faces in the dorsal direction within the epidural space. Such misalignment of the ventral electrodes may result in a casting of electrical impulses in the dorsal direction rather than in the desired spinal paresthesia inducing ventral direction. Such dorsally directed electrical pulses may undesirably produce localized back pain without producing any palliative pain reducing effect upon the spinal cord.

To prevent such arm rotation induced palliative treatment failures, the instant invention's electrical pulse generating means are preferably adapted for alternatively exclusively electrifying the dorsal matrix of electrical conductors. Accordingly, upon an occurrence of the above described electrode series rotating inversion, the electrical pulse generating means may be alternatively operated to exclusively electrify the dorsal electrodes which have been found to be ventrally oriented.

Upon final implantation of the instant inventive assembly at the target spinal location, the distal end of the lateral arm tends to ventrally bias against the dura mater in the manner of a rotation stopping arm. Regardless of whether a misaligning rotation of the assembly has occurred during deployment, the distal end of the arm operates for prevention of further misaligning rotations, and the pulse generating means may be operated to exclusive electrify either the ventral or dorsal electrodes as dictated by the electrodes' finally implanted orientations.

In a preferred embodiment of the instant inventive assembly, an oppositely-lateral or leftwardly extending arm is additionally provided. Similarly with the lateral arm component, the oppositely lateral arm preferably supports oppositely lateral portions of the dorsal and ventral electrodes series. Where such oppositely lateral arm is provided, the dorsal and ventral matrices of electrical conductors may additionally be housed by and extend through such arm. The instant invention's preferred provision of both lateral and oppositely lateral rotation stopping arms advantageously provides additional stability against any undesirable rotation of the assembly following implantation.

Accordingly, objects of the instant invention include the provision of intellectual assembly for stimulation of a spinal cord which incorporates structures, as described above, and which arranges those structures in relation to each other, in manners described above for the achievement of beneficial functions, as described above.

Other and further objects, benefits, and advantages of the instant invention will become known to those skilled in the art upon review of the Detailed Description which follows, and upon review of the appended drawings.

DETAILED DESCRIPTION OF A PREFERRED EMBODIMENT

Figure 1:
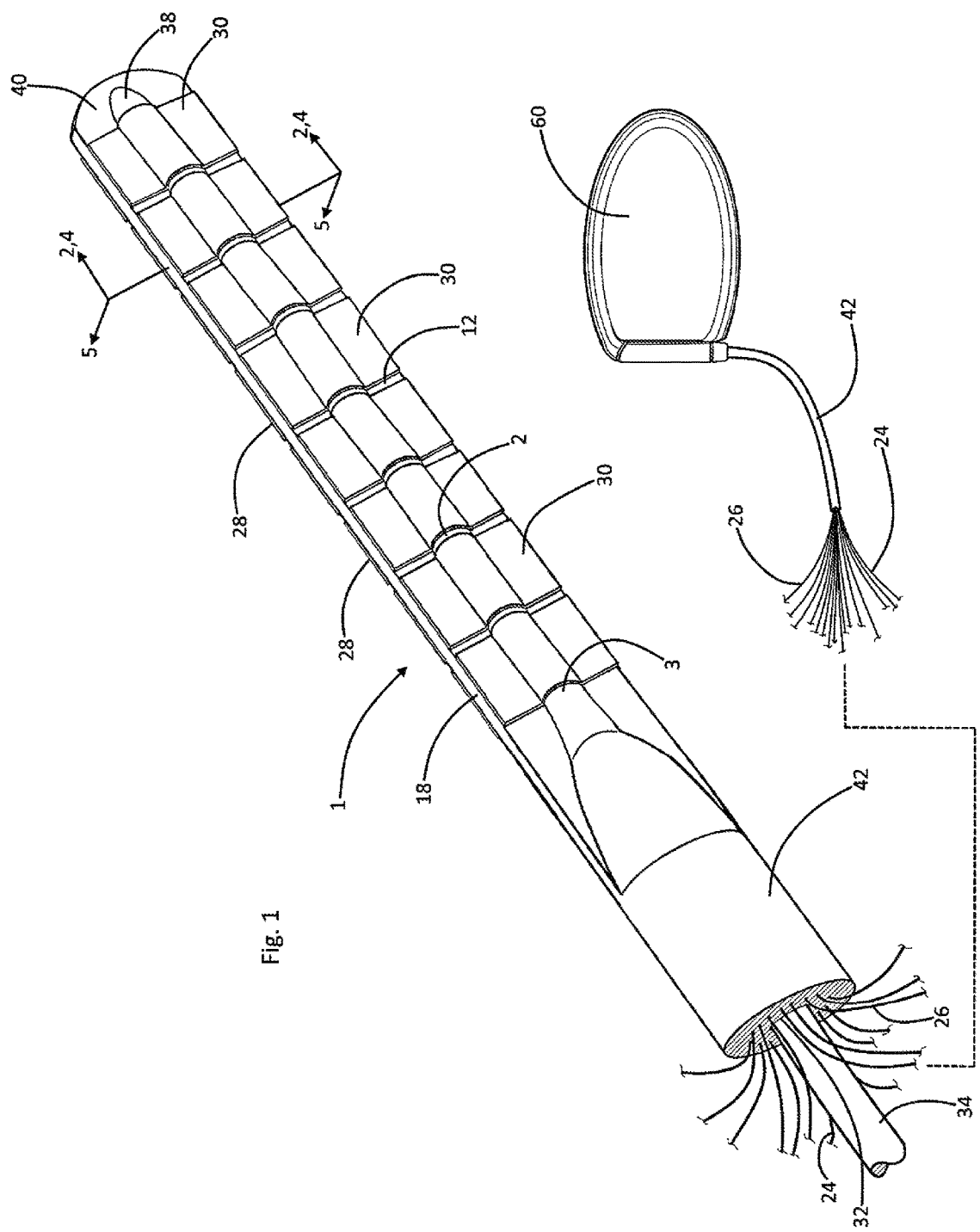
FIG. 1 is a perspective view of a preferred embodiment of the instant inventive electrode assembly for stimulation of a spinal cord.
Figure 2:
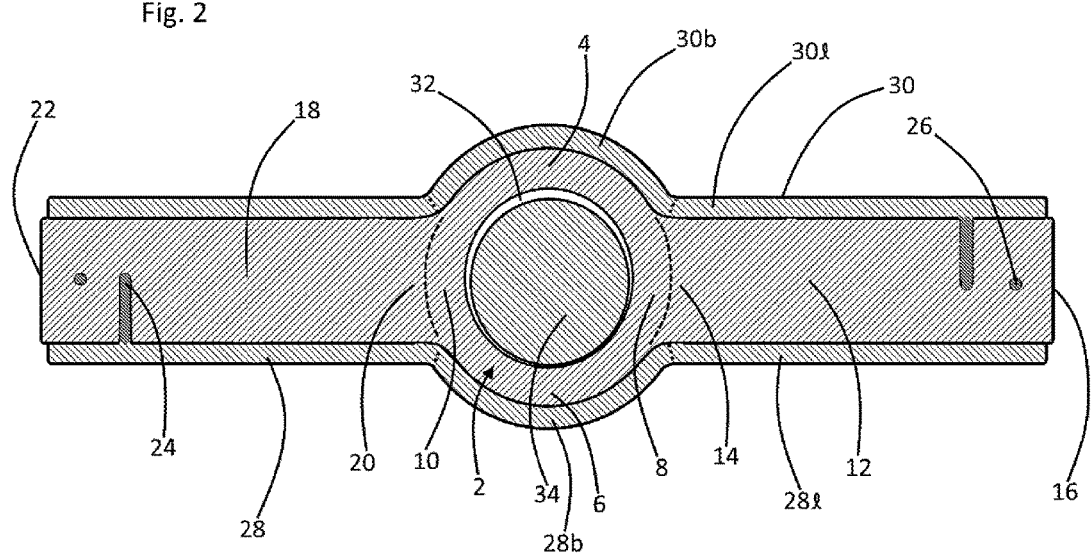
FIG. 2 is a sectional view, as indicated in FIG. 1.

Referring now to the drawings and in particular to Drawing FIG. 1, a preferred embodiment of the instant inventive electrode assembly for stimulation of a spinal cord is referred to generally by Reference Arrow 1. Referring further simultaneously to FIG. 2, the assembly 1 preferably comprises a base component 2 which has a posterior end 3, such base 2 extending anteriorly from such posterior end 3 to the assembly's anterior end 40. The base 2 has a dorsal side 4, a ventral side 6, a lateral or rightward side 8, and an oppositely-lateral or leftward side 10. In the preferred embodiment, the base component 2 is composed of a durable and flexible plastic material which has a high dielectric strength for electrically isolating attached and supported conductors described below.

The instant inventive assembly 1 preferably further comprises a lateral arm component 12 which is preferably formed of the same plastic material as the base 2. The lateral arm 12 has a proximal end 14 and a distal end 16, the proximal end 14 being fixedly attached to or wholly formed with the lateral side 8 of the base 2. Such wholly formed attachment is represented by the curved dashed line drawn between the base lateral side 8 and the proximal end 14 of arm 12.

Further structural components of the instant inventive assembly comprise a ventral series of electrodes 28 which are fixedly attached to a surface selected from the group consisting of the ventral side 6 of the base 2, and the ventral side of the lateral arm 12. As is particularly shown in Drawing FIG. 2, ventral electrode 28 has a lateral or rightward portion 28*l* which is fixedly attached to the ventral surface of lateral arm 12. Such ventral electrode 28 preferably has a further portion 28*b* which is similarly fixedly attached to the ventral side 6 of the base component 2. While the ventral electrode 28 is preferably sized and positioned for fixed attachment to both the lateral arm 12 and the base 2, such connection may suitably reside at and span over only the ventral aspect of the base 2 or, alternatively, only over the ventral aspect of the lateral arm 12.

As shown in Drawing FIG. 1, the lateral arm 12 preferably extends longitudinally from the posterior end 3 of the base 2 to the base's anterior end, and such arm's ventral electrodes 28 are preferably intermittently spaced therealong. In the preferred embodiment, the ventral electrodes 28 are composed of a durable, corrosion resistant, and electrically conductive material such as platinum, and such electrodes are preferably bonded to the dorsally overlying plastic structures 6 and 12 via an adhesive bond or via integral molding.

A further structural component of the instant inventive assembly comprises a dorsal series of electrodes 30 which is, similarly with the ventral series of electrodes 28, fixedly attached to a surface selected from the group consisting of the base's dorsal side 4, and the dorsal side of the lateral arm 12. Similarly with the underlying ventral electrodes 28, the dorsal electrodes 30 may comprise either lateral arm attached portions 30*l* or base attached portions 30*b*, while a preferred embodiment extends and attaches each dorsal electrode 30 to both of such structures.

Further structural components of the instant inventive assembly comprise ventral and dorsal matrices of electrical conductors or wires 24 and 26. In the preferred embodiment, each electrical conductor among the ventral matrix of electrical conductors 24 extends to and electrically communicates with one and only one of the electrodes among the ventral electrode series 28. Correspondingly, each conductor among the dorsal matrix of electrical conductors 26 extends to and electrically communicates with one and only one of the dorsal electrodes 30. As the ventral and dorsal matrices of electrical conductors 24 and 26 extend longitudinally through arm 12 and/or through base 2 for electrical communications with the electrodes 28 and 30, such conductors are preferably insulated and electrically isolated from each other by the preferably plastic dielectric material of the lateral arm 12 and base 2.

Further structural components of the instant inventive assembly comprise means for electrifying and communicating electrical pulses along the matrices of electrical conductors 24 and 26. In the preferred embodiment, such means comprise a subcutaneously implanted battery powered electric pulse generator 60 which includes a flexible wire lead 42, such lead containing and posteriorly extending the matrices of conductors 24 and 26. In the preferred embodiment, such pulse generator 60 is programmable and operable for exclusively transmitting electric pulses to conductor matrix 24 or, alternatively, to conductor matrix 26. The implantable electric pulse generator 60 is intended as being representative of other types of electric pulse generators such as external electric pulse generators.

Figure 5:
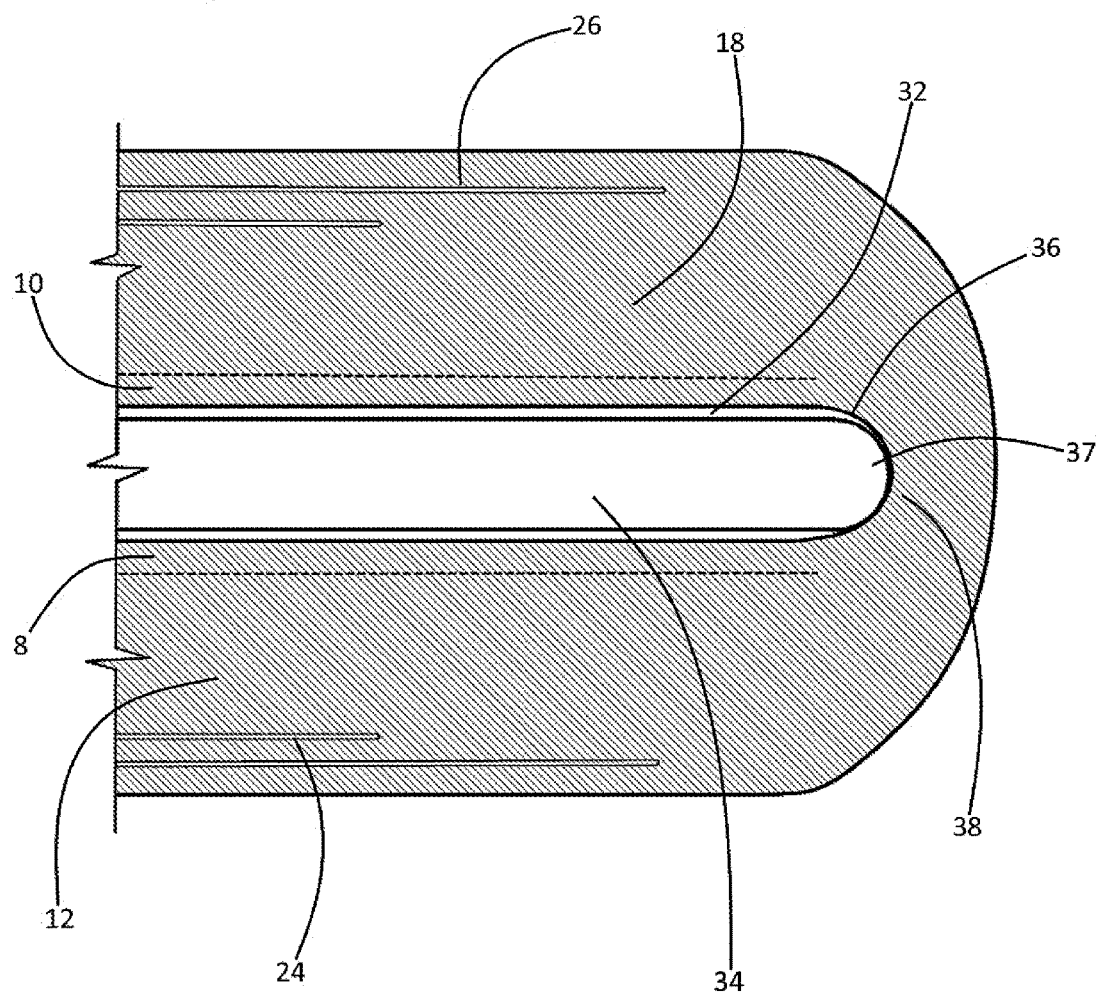
FIG. 5 is an alternative sectional view, as indicated in FIG. 1.

The flexible and preferably plastic lead 42 is fixedly attached to and extends posteriorly from the posterior ends of the base 2 and the lateral arm 12. Such flexible lead 42 preferably encases both conductor matrices 24 and 26 within its insulating plastic matrix. The base 2 and the attached and posteriorly extending lead 42 preferably forms and defines an interior hollow socket or bore 32 which is covered at its anterior end by (referring to FIG. 5) a cap 38, such cap having an interior anteriorly facing ceiling 36.

To assist in spinal implantation of the assembly 1, the hollow bore 32 preferably temporarily slidably receives a flexible stainless steel stay 34. Such stay 34 may be extended along the hollow bore 32 in the anterior direction until the anterior end 37 of the stay 34 engages ceiling 36. Thereafter, a pushing force may be applied by a physician simultaneously against the lead 42 and against the stay 34. Such pushing force initially extends the assembly 1 through the interior bore of a Tuohy needle or cannula (not pictured within views) whose tissue lancing tip angularly extends into, referring in particular to FIG. 3, the pain patient's dorsal epidural space 48 beneath the patient's dorsal spinous process 43. The selected Tuohy needle preferably has a narrow interior diameter, approximating 1.4 millimeters, and the lateral to oppositely lateral dimension of the electrode assembly is preferably closely fitted for sliding passage therethrough.

During such Tuohy needle assisted implantation of the instant inventive assembly 1, the anterior end 40 of the assembly is typically driven in the anterior direction by the anterior end 37 of the stay 34. Such driving action moves the assembly 1 along and through the dorsal aspect of the pain patient's spinal epidural space 48. During passage therethrough, such anterior end 40 progressively impinges against and lances through adipose and veinous tissues within the epidural space 48.

Figure 3:
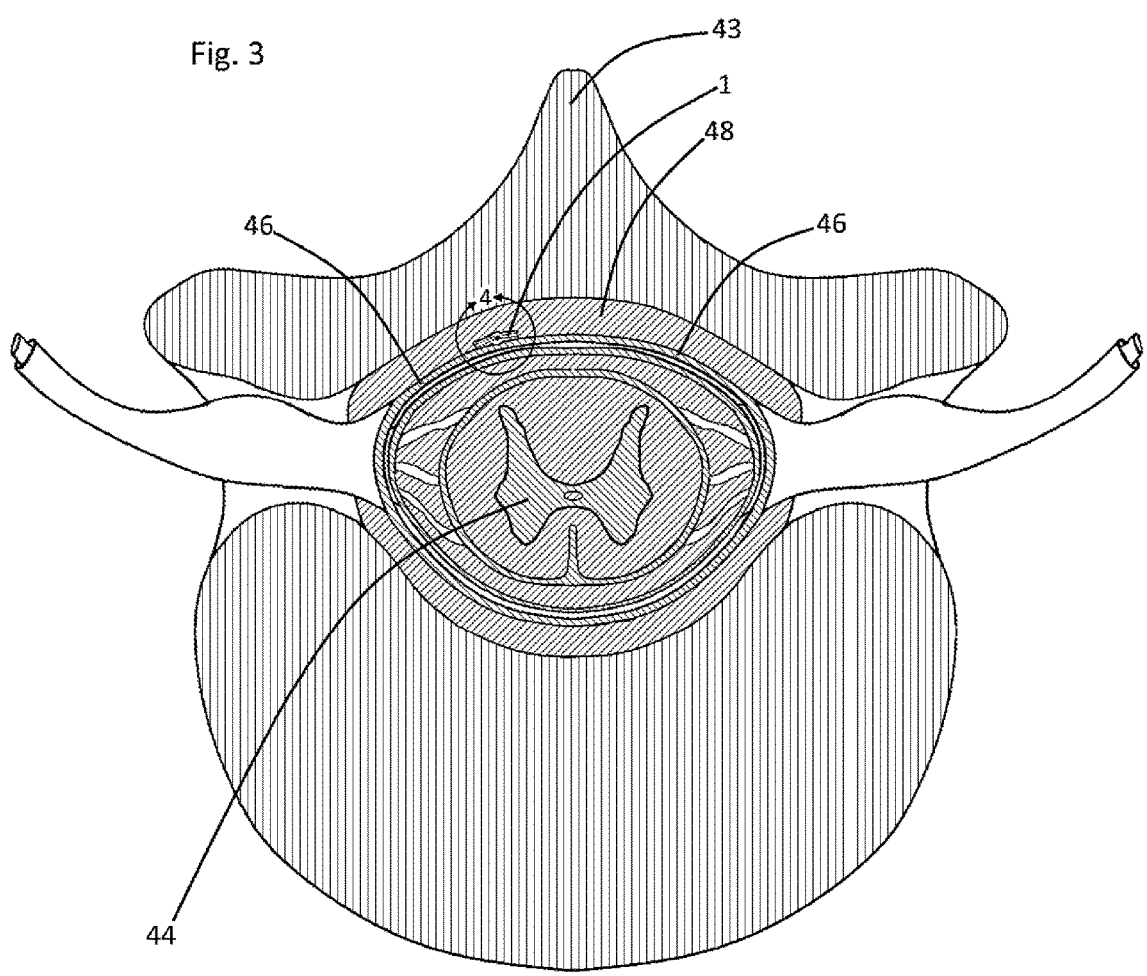
FIG. 3 redepicts the structure of FIG. 2, the view of FIG. 3 further showing such structure implanted dorsally over a pain patient's spinal cord and within the pain patient's spinal epidural space.
Figure 4:
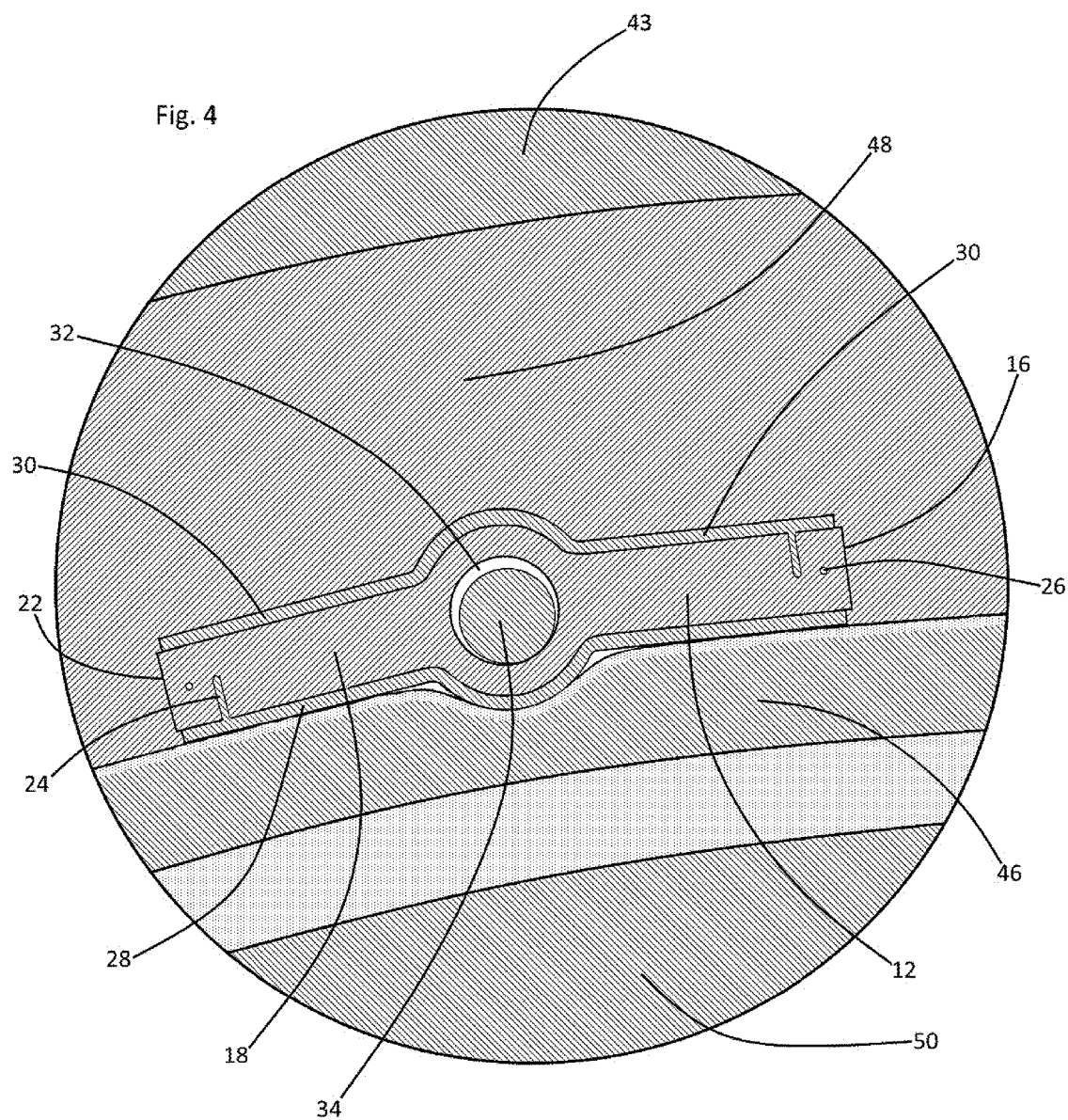
FIG. 4 is a magnified partial view as indicated in FIG. 3.

Upon arriving at a target location which dorsally overlies the patient's spinal cord 44, the assembly 1 may advantageously be oriented as indicated in FIGS. 3 and 4 with its ventral electrode series 28 facing ventrally toward the patient's ventrally underlying spinal cord 44. In such orientation, the ventral contact faces of the ventral electrode series 28 advantageously abut and electrically ground against the dorsal surface of the dura mater 46. Upon such contact, electrical pulses communicated to the electrodes 28 advantageously emanate ventrally through the dura mater 46, across an arachnoid tissue layer 50, and into the spinal cord 44 for the production of a desirable pain signal blocking or masking paresthesia.

Progressive lancing impingements of the anterior end 40 against adipose and veinous tissues within the epidural space 48 during spinal deployment of the assembly 1 may, on occasion impart rotations to the assembly 1. Accordingly, upon arrival at the target implantation site indicated by FIG. 3, the ventral electrodes 28 may not face in the ventral direction for inducement of the desired paresthesia effect. In such event, the pulse generator 60 may be alternatively operated to exclusively transmit electrical pulses to the dorsal electrodes 30.

Regardless of which series among the electrode series 28 and 30 becomes initially oriented in the correct ventral direction upon implantation at the target site, the distal end 16 of the lateral arm 12 operates as a rotation stop which resists further disorientation rotations of the assembly 1. Scar tissue healing surrounding the assembly 1 tends to securely hold the assembly at the initially implanted orientation.

In a preferred embodiment of the instant invention, the assembly 1 additionally comprises an oppositely-lateral arm 18 whose proximal end 20 is fixedly attached to or formed wholly with the oppositely-lateral side 10 of the base 2. The provision of such oppositely-lateral arm 18 advantageously provides an additional rotation stopping arm distal end 22, and allows the base 2 to be axially and centrally positioned with respect to arms 12 and 18. The provision of such opposite arm also allows for conductor extensions therethrough. As shown in FIG. 2, the ventral and dorsal electrode series 28 and 30 preferably extend oppositely laterally to the distal end 22 of arm 18. In order to accommodate utilization of a stay 34 having a diameter approximating the thicknesses of arms 12 and 18, the dorsal and ventral sides 4 and 6 of the base 2 preferably protrude arcuately dorsally and ventrally.

Upon the preferred provision of the oppositely lateral arm 18, such arm in combination with the base 2 and the lateral arm 12 constitutes a first plastic matrix which receives and supports the anterior ends of the dorsal and ventral conductors 26 and 24. In relation with such first plastic matrix, the plastic lead 42 constitutes a second plastic matrix which is formed continuously with the first plastic matrix and which receives the supports the posterior extensions of those conductors.

While the principles of the invention have been made clear in the above illustrative embodiment, those skilled in the art may make modifications to the structure, arrangement, portions and components of the invention without departing from those principles. Accordingly, it is intended that the description and drawings be interpreted as illustrative and not in the limiting sense, and that the invention be given a scope commensurate with the appended claims.

The invention hereby claimed is:

1. An electrode assembly for stimulation of a spinal cord within a spinal canal, the spinal canal containing a dura mater dorsally overlying the spinal cord, said assembly comprising:
    (a) a base having an anterior and posterior ends, having lateral and oppositely lateral sides, and having dorsal and ventral sides;
    (b) a lateral arm having anterior and posterior ends, having dorsal and ventral sides, and having proximal and distal ends, wherein said arm's proximal end is fixedly attached to the base's lateral side;
    (c) a ventral series of electrodes fixedly attached to a surface selected from the group consisting of the base's ventral side and the lateral arm's ventral side;
    (d) a dorsal series of electrodes fixedly attached to a surface selected from the group consisting of the base's dorsal side and the lateral arm's dorsal side;
    (e) ventral and dorsal matrices of electrical conductors, said matrices respectively communicating electrically with the ventral and dorsal series of electrodes; and
    (f) means for electrifying the ventral and dorsal matrices of electrical conductors, said means being adapted for, upon a rotation stopping contact by the distal end of the lateral arm against the dura mater, exclusively electrifying the ventral matrix of electrical conductors, said means being further adapted for, upon a counter-rotation stopping contact by the distal end of the lateral arm against the dura mater, exclusively electrifying the dorsal matrix of electrical conductors.

2. The electrode assembly of claim 1 further comprising an oppositely lateral arm having anterior and posterior ends, the oppositely lateral arm further having proximal and distal ends wherein the proximal end is fixedly attached to the base's oppositely-lateral side, the oppositely-lateral arm further having dorsal and ventral sides, wherein the ventral series of electrodes is further fixedly attached to the ventral side of the oppositely lateral arm, and wherein the dorsal series of electrodes is further fixedly attached to the dorsal side of the oppositely-lateral arm.

3. The electrode assembly of claim 2 further comprising a socket having an anterior ceiling, said socket having a hollow bore which is positioned between the base's dorsal and ventral sides and which extends posteriorly from the ceiling.

4. The electrode assembly of claim 3 wherein the base and the lateral and oppositely lateral arms comprise a first plastic matrix, and wherein the ventral and dorsal matrices of electrical conductors are contained within said first matrix.

5. The electrode assembly of claim 4 further comprising a flexible lead fixedly attached to and extending posteriorly from the posterior end of the base.

6. The electrode assembly of claim 5 wherein the socket's posteriorial extension comprises a hollow bore.

7. The electrode assembly of claim 6 wherein the flexible lead comprises a second plastic matrix, wherein the second plastic matrix is continuous with the first plastic matrix.

8. The electrode assembly of claim 7 wherein the ventral and dorsal matrices of electrical conductors are further contained within the second plastic matrix.

9. The electrode assembly of claim 8 further comprising a cap fixedly attached to the anterior end of the base, wherein the socket's ceiling comprises a posterior surface of said cap.

10. The electrode assembly of claim 9 further comprising an insertion stay having an anterior end, said stay being slidably receivable within the socket for driving contact of said anterior end against the anterior ceiling.

* * * * *